United States Patent [19]

Scherm et al.

[11] 4,370,330
[45] Jan. 25, 1983

[54] METHOD OF ENHANCING CIRCULATION WITH PIPERAZINES

[75] Inventors: Arthur Scherm, Bad Homburg; Dezsoe Peteri, Hattersheim, both of Fed. Rep. of Germany

[73] Assignee: Merz & Company, Frankfurt, Fed. Rep. of Germany

[21] Appl. No.: 308,607

[22] Filed: Oct. 5, 1981

Related U.S. Application Data

[62] Division of Ser. No. 181,189, Aug. 22, 1980.

[30] Foreign Application Priority Data

Aug. 25, 1979 [DE] Fed. Rep. of Germany ....... 2934450
Aug. 25, 1979 [DE] Fed. Rep. of Germany ....... 2934488

[51] Int. Cl.³ .................. A61K 31/495; C07D 295/08
[52] U.S. Cl. ..................................... 424/250; 544/394
[58] Field of Search ......................................... 424/250

[56] References Cited

FOREIGN PATENT DOCUMENTS 868353 5/1961 United Kingdom .

Primary Examiner—Anton H. Sutto
Attorney, Agent, or Firm—Gordon W. Hueschen

[57] ABSTRACT

Novel N-(trimethoxybenzyl)-piperazines of the formula:

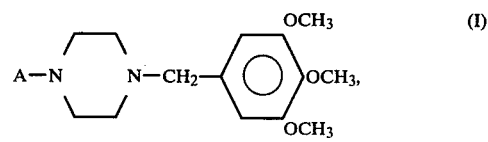

(I)

wherein A =

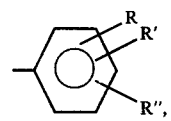

wherein
R is trifluoromethyl, hydroxy, nitro, halogen, lower-alkyl, or lower-alkoxy;
R' is hydrogen, trifluoromethyl, halogen, lower-alkyl, or lower-alkoxy;
R" is hydrogen or lower-alkoxy,
or wherein R and either R' or R" together stand for lower-alkylene dioxy, and acid addition salts thereof, a method of preparing same, pharmaceutical compositions thereof, and a method of enhancing circulation, especially cerebrovascular circulation, therewith, are disclosed.

36 Claims, No Drawings

METHOD OF ENHANCING CIRCULATION WITH PIPERAZINES

This is a division of application Ser. No. 181,189, filed Aug. 22, 1980.

BACKGROUND OF THE INVENTION

(1) Field of Invention

Circulation-enhancing drugs, substituted piperazine compounds useful for said purpose, preparation thereof, compositions containing the same, and method of using the same for the said purpose.

(2) Prior Art

Upon comparison with the known and accepted Cinnarizine (Arch. Int. Pharmacodyn. Ther. 204, 37, 1973), a known circulation stimulant, the piperazines according to the invention show a superior circulation-enhancing action, especially in the brain. When contrasted with the disubstituted benzyl piperazines reported to have adrenolytic or antihistaminic action in J. Med. Chem. 6 (5), 1963, pages 541–544, the compounds according to the invention have been found to be characterized by a strong circulation-enhancing action, especially on the cerebrovascular system. Although the N-substituted trialkylbenzyl piperazines known from DE-OS No. 27 14 996 are reported to have cardiovascular properties, they cannot be compared with the compounds according to the invention, either with regard to chemical constitution or with regard to action. The same statement is true with respect to the more complex substituted piperazines of DE-OS No. 25 11 022. See also Chemical Abstracts 59 (1963), items 12804b and 12825e, for abstracts of the J. Med. Chem. article and the corresponding French Pat. No. 1,318,449.

OBJECTS OF THE INVENTION

It is an object of the present invention to provide novel circulation-enhancing compounds. It is a further object of the present invention to provide certain novel N-(trimethoxybenzyl)-piperazines which are useful as circulation-enhancing agents. It is a further object of the invention to provide a method for the preparation of such compounds, pharmaceutical compositions of such compounds, and a method of using the said novel compounds for the said circulation-enhancing purpose. Additional objects will become apparent hereinafter, and still other objects will be apparent to one skilled in the art to which this invention appertains.

SUMMARY OF THE INVENTION

Novel N-(trimethoxybenzyl)-piperazines of the formula:

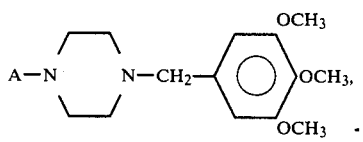

wherein A =

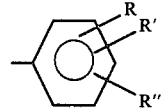

wherein
R is trifluoromethyl, hydroxy, nitro, halogen, lower-alkyl, or lower-alkoxy;
R' is hydrogen, trifluoromethyl, halogen, lower-alkyl, or lower-alkoxy;
R" is hydrogen or lower-alkoxy,
or wherein R and either R' or R" together stand for lower-alkylene dioxy, and acid addition salts thereof, a method of preparing same, pharmaceutical compositions thereof, and a method of enhancing circulation, especially cerebrovascular circulation, therewith, are the subject of the present invention.

These N-(trimethoxybenzyl)-piperazines of the foregoing general formula, including their inorganic and organic acid addition salts, have been prepared and found to possess a marked stimulating action on mammalian circulation, especially cerebrovascular blood supply, do not show untoward side-effects, and may therefore be beneficially employed in human and veterinary medicine. They may be administered orally, e.g., as tablets, capsules, syrups, or solutions, or by the parenteral route, preferably in the form of a water-soluble salt. They are also suitable for combination with other drugs which act upon the vascular system, such as nicotinic acid and its esters, or with other active pharmaceutical principles.

IN GENERAL

Preferably, in the foregoing formula, lower-alkyl and lower-alkoxy comprise from one to four carbon atoms, inclusive, and preferably halogen comprises fluorine and chlorine, and lower-alkylene dioxy comprises one through four carbon atoms in the alkylene group. Other lower-alkyl, lower-alkoxy, halogen, and lower-alkylene atoms or groups may be present in the compounds of the invention, but are not preferred. Lower-alkyl and lower-alkoxy may, as usual, have from one to eight carbon atoms, inclusive; halogen may, as usual, include not only chlorine and fluorine, but also bromine and iodine; and lower-alkylene may, as usual, include methylene through octylene groups. However, as previously stated, fluorine and chlorine are preferred, lower-alkyl such as methyl, ethyl, propyl, isopropyl, butyl, isobutyl, and so on, are preferred, methoxy, ethoxy, propoxy, isopropoxy, butoxy, and the like are preferred, and methylene, ethylene, propylene, and butylene are similarly preferred in the alkylene substituent. Still more particularly, among the groups preferred for R are the following: fluorine, methyl, methoxy, ethyl, ethoxy, hydroxy, chloro, nitro, and trifluoromethyl. Preferred groups within the scope of R' are: trifluoromethyl, chloro, methyl, methoxy, and hydrogen. Preferred groups within the scope of R" are: methoxy and hydrogen. As already indicated, when the substituent R and either R' or R" are located on adjacent carbon atoms of the phenyl ring, another preferred substituent may be methylenedioxy. Further, of the compounds of the present invention, those having at least two substituents in the phenyl group constituting the radical "A", as well as those compounds wherein the said phenyl radical is monosubstituted with a substituent other than lower-alkyl, are preferred, in which case the trifluoromethyl, fluoro, chloro, methoxy, ethoxy, and hydroxy substituents are especially preferred.

MANUFACTURING PROCESS

The new N-(trimethoxybenzyl)-piperazines according to the invention can be manufactured according to either of two procedures, as outlined generally hereinafter and employed specifically in the Examples which follow.

Method A

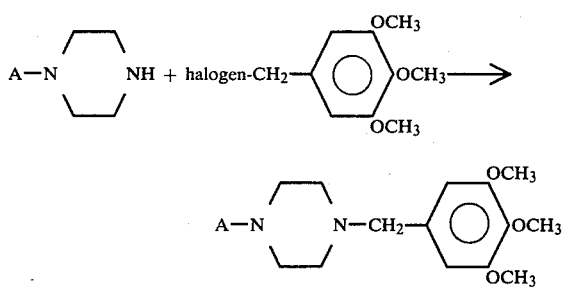

Equimolar volumes of 3,4,5-trimethoxybenzyl halide, e.g., bromide or chloride, the selected substituted N-phenylpiperazine, an acid-binding agent such as sodium carbonate, sodium bicarbonate, triethylamine, or an excess of the basic component, are dissolved or suspended in a solvent such as dimethyl formamide. The reaction takes place upon heating at elevated temperature, preferably under reflux, within a few hours. Insoluble matter is removed by filtration, centrifugation, or decantation, and the solvent is evaporated. The residue is recrystallized from a suitable solvent or, if an acid addition salt is desired to be produced, the crude reaction product is mixed with the respective acid, the resulting salt being recrystallized from a suitable solvent. The yields by this method range between 40 and 90% of the theoretical value.

Method B

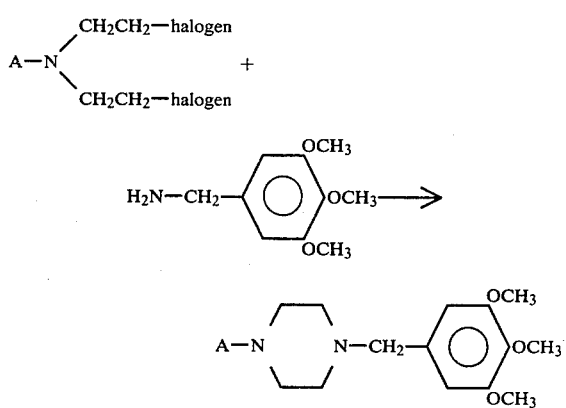

One mol of the selected substituted N,N-bis(2-halo, e.g., bromo or chloroethyl)aniline is heated, preferably with an excess, e.g., 1.5 to 2.5 mol, of 3,4,5-trimethoxybenzylamine at an elevated temperature, e.g., to about 50°-180° C. With preparations which can be stirred only with difficulty and/or which tend to darkening, an inert diluent, e.g., diphenyl, may be used, or a high-boiling hydrocarbon mixture and/or an inert protective gas such as nitrogen may be employed.

After a reaction time of 2-24 hours, the reaction mixture is allowed to cool and, after addition of base, e.g., NaOH, the unreacted 3,4,5-trimethoxybenzylamine and, if necessary, the diluent is distilled over.

After appropriate purification, the amine may be used again. Further processing of the starting material may be carried out according to Method A. The yields are 40-95% of the theoretical value, based upon the N,N-bis(2-haloethyl)aniline employed.

The exact solvent, reaction temperature, and the exact reaction time is not critical according to either procedure except for attainment of maximum yields and conversions.

DETAILED DESCRIPTION OF THE INVENTION

The following Examples are given by way of illustration only, but are not to be construed as limiting.

EXAMPLE 1

3.53 g of N-(4-fluorophenyl)-N,N-bis-(2-chloroethyl)-amine and 7 g of 3,4,5-trimethoxybenzyl amine is heated to 120° C. for 8 hours under $N_2$ atmosphere. After cooling of the reaction mixture 50 ml of 1 N NaOH is added, and the excess 3,4,5-trimethoxybenzyl amine removed by distillation with steam.

After drying of the residue by steam, it is mixed with methanol and hydrochloric acid gas introduced in the solution. After sucking off and drying of the resulting precipitate, 3.6 g of N-(3,4,5-trimethoxy-benzyl)-N'-(4-fluorophenyl)-piperazine hydrochloride is obtained. Mp: 270° C.

Elementary analysis: C—calculated: 60.52%, found: 60.42%. H—calculated: 6.60%, found: 6.48%. N—calculated: 7.06%, found: 6.96%. Cl—calculated: 8.93%, found: 8.88%.

EXAMPLE 2

8.66 g of 3,4,5-trimethoxybenzyl chloride, 7.05 g of N-(2-methylphenyl)-piperazine and 7.00 g of finely-powdered KOH is boiled for 8 hours in 50 ml of dimethyl formamide under reflux.

After sucking off insoluble matter the filtrate is evaporated to dryness, the residue is dissolved in methanol, hydrochloric acid gas is introduced into the solution and the precipitate sucked off. 8.00 g of N-(3,4,5-trimethoxybenzyl)-N'-(2-methylphenyl)-piperazine is obtained. Mp.: 89° C.

Elementary analysis: C—calculated: 70.76%, found: 70.96%. H—calculated: 7.92%, found: 7.88%. N—calculated: 7.86%, found: 7.87%.

The hydrochloride is obtained by redissolving the free base and further treatment with hydrogen chloride.

EXAMPLE 3

8.66 g of 3,4,5-trimethoxybenzyl chloride and 7.73 g of N-(3-methoxyphenyl)-piperazine and 7.00 g of $K_2CO_3$ is reacted and processed according to example 2.

8.00 g of N-(3,4,5-trimethoxy-benzyl)-N'-(3-methoxyphenyl)-piperazine hydrochloride is obtained. Mp.: 242° C.

Elementary analysis: C—calculated: 61.68%, found: 61.30%. H—calculated: 7.15%, found: 7.01%. N—calculated: 6.85%, found: 6.73%. Cl—calculated: 8.67%, found: 8.63%.

EXAMPLE 4

8.3 g of 3,4,5-trimethoxybenzyl chloride and 3.8 g of N-(2-ethylphenyl)-piperazine and 3.5 g of $K_2CO_3$ are reacted and processed according to example 2. 6.5 g of N-(3,4,5-trimethoxy-benzyl)-N'-(2-ethylphenyl)-piperazine dihydrochloride is obtained. Mp.: 179° C.

Elementary analysis: C—calculated: 59.65%, found: 59.45%. H—calculated: 7.28%, found: 7.26%. N—calculated: 6.32%, found: 6.24%. Cl—calculated: 16.00%, found: 15.90%.

EXAMPLE 5

8.3 g of 3,4,5-trimethoxybenzyl chloride and 4.1 g of N-(2-ethoxyphenyl)-piperazine and 3.5 g of $K_2CO_3$ are reacted and processed according to example 2. 7.2 g of N-(3,4,5-trimethoxy-benzyl)-N'-(2-ethoxyphenyl)-piperazine dihydrochloride is obtained. Mp.: 212° C.

Elementary analysis: C—calculated: 57.52%, found: 57.34%. H—calculated: 7.02%, found: 6.82%. N—calculated: 6.10%, found 6.01%. Cl—calculated: 15.43%, found: 15.63%.

EXAMPLE 6

8.3 g of 3,4,5-trimethoxybenzyl chloride and 4.15 g of N-(2-nitrophenyl)-piperazine and 3.5 g of $K_2CO_3$ are reacted and processed according to example 2. 5.5 g of N-(3,4,5-trimethoxy-benzyl)-N'-(2-nitrophenyl)-piperazine hydrochloride is obtained. Mp.: 248° C.

Elementary analysis: C—calculated: 56.67%, found: 56.68%. H—calculated: 6.18%, found: 6.20%. N—calculated: 9.91%, found: 9.92%. Cl—calculated: 8.36%, found: 8.53%.

EXAMPLE 7

8.3 g of 3,4,5-trimethoxybenzyl chloride and 3.5 g of N-(4-hydroxyphenyl)-piperazine and 3.5 g of $K_2CO_3$ are reacted and processed according to example 2. 4.2 g of N-(3,4,5-trimethoxy-benzyl)-N'-(4-hydroxyphenyl)-piperazine hydrochloride is obtained. Mp.: 268° C. (decomposition).

Elementary analysis: C—calculated: 60.83%, found: 61.02%. H—calculated: 6.88%, found: 6.75%. N—calculated: 7.09%, found: 7.16%. Cl—calculated: 8.98%, found: 9.14%.

EXAMPLE 8

4.33 g of 3,4,5-trimethoxybenzyl chloride and 3.93 g of N-(2-chlorophenyl)-piperazine and 3.5 g of $K_2CO_3$ are reacted and processed according to example 2. 5.0 g of N-(3,4,5-trimethoxy-benzyl)-N'-(2-chlorophenyl)-piperazine dihydrochloride is obtained. Mp.: 225° C.

Elementary analysis: C—calculated: 58.12%, found: 57.99%. H—calculated: 6.34%, found: 6.25%. N—calculated: 6.78%, found: 6.69%. Cl—calculated: 17.15%, found: 17.02%.

EXAMPLE 9

3.85 g of N-(2-methoxyphenyl)-piperazine, 4.33 g of 3,4,5-trimethoxybenzyl chloride and 3.5 g of $K_2CO_3$ are reacted and processed according to example 2. 5.0 g of N-(3,4,5-trimethoxy-benzyl)-N'-(2-methoxyphenyl)-piperazine dihydrochloride is obtained. Mp.: 219° C.

Elementary analysis: C—calculated: 56.63%, found: 56.72%. H—calculated: 6.79%, found: 6.76%. N—calculated: 6.29%, found: 6.28%. Cl—calculated: 15.92%, found: 15.91%.

EXAMPLE 10

3.85 g of N-(4-methoxyphenyl)-piperazine, 4.33 g of 3,4,5-trimethoxybenzyl chloride and 3.5 g of $K_2CO_3$ are reacted and processed according to example 2. 4.5 g of N-(3,4,5-trimethoxy-benzyl)-N'-(4-methoxyphenyl)-piperazine dihydrochloride is obtained. Mp.: 242° C.

Elementary analysis: C—calculated: 56.63%, found: 55.60%. H—calculated: 6.79%, found: 6.57%. N—calculated: 6.29%, found: 6.94%. Cl—calculated: 15.92%, found: 15.42%.

EXAMPLE 11

3.53 g of N-(2-fluorophenyl)-N,N-bis-(2-chloroethyl)-amine and 7 g of 3,4,5-trimethoxybenzyl amine are reacted and processed according to example 1.

3.5 g of N-(3,4,5-trimethoxy-benzyl)-N'-(2-fluorophenyl)-piperazine hydrochloride is obtained. Mp.: 240° C.

Elementary analysis: C—calculated: 60.54%, found: 60.42%. H—calculated: 6.60%, found: 6.48%. N—calculated: 7.06%, found: 6.96%. Cl—calculated: 8.93%, found: 8.88%.

EXAMPLE 12

8.66 g of 3,4,5-trimethoxybenzyl chloride, 7.05 g of N-(3-methylphenyl)-piperazine and 7.00 g of finely powdered KOH are reacted and processed according to example 2.

8.00 g of N-(3,4,5-trimethoxy-benzyl)-N'-(3-methylphenyl)-piperazine hydrochloride is obtained. Mp.: 251° C.

Elementary analysis: C—calculated: 64.19%, found: 64.30%. H—calculated: 7.44%, found: 7.46%. N—calculated: 7.13%, found: 7.09%. Cl—calculated: 9.02%, found: 8.86%.

EXAMPLE 13

8.66 g of 3,4,5-trimethoxybenzyl chloride, 7.05 g of N-(4-methylphenyl)-piperazine and 7.00 g of finely powdered KOH are reacted and processed according to example 2.

8.00 g of N-(3,4,5-trimethoxy-benzoyl)-N'-(4-methylphenyl)-piperazine hydrochloride is obtained. Mp: 255° C.

Elementary analysis: C—calculated: 64.19%, found: 64.44%. H—calculated: 7.44%, found: 7.41%. N—calculated: 7.13%, found: 7.14%. Cl—calculated: 9.02%, found: 8.88%.

EXAMPLE 14

50 ml of dimethyl formamide, 8.64 g of 3,4,5-trimethoxybenzyl chloride, 7.60 g of N-(3,4-dimethylphenyl)-piperazine and 7.00 g of $K_2CO_3$ are boiled for 8 hours under reflux. After sucking off insoluble matter the filtrate is evaporated to dryness and the residue is dissolved in methanol. Subsequently hydrochloric acid gas is introduced in the solution and the precipitate sucked off. After drying 10.4 g of N-(3,4,5-trimethoxybenzyl)-N'-(3,4-dimethylphenyl)-piperazine hydrochloride. Mp: 242° C.

Elementary analysis: C—calculated: 64.92%, found: 64.61%. H—calculated: 7.68%, found: 7.94%. N—calculated: 6.88%, found: 6.70%. Cl—calculated: 8.71%, found: 8.86%.

EXAMPLE 15

3.23 g of N-(3-trifluoromethyl-4-chlorophenyl)-N,N-bis-(2-chloroethyl)-amine and 7 g of 3,4,5-trimethoxybenzyl amine are heated to 120° C. under $N_2$ atmosphere for 8 hours. After cooling of the reaction mixture 50 ml of 1 N NaOH is added, excess 3,4,5-trimethoxybenzyl amine being removed by distillation by steam.

After evaporation of the residue to dryness it is mixed with methanol, and hydrochloric acid gas is introduced in the solution.

After sucking off and drying the resulting precipitate, 3.6 g of N-(3,4,5-trimethoxy-benzyl)-N'-(3-trifluoromethyl-4-chlorophenyl)-piperazine hydrochloride is obtained. Mp. 228° C.

Elementary analysis: C—calculated: 52.39%, found: 52.22%. H—calculated: 5.23%, found: 5.20%. N—calculated: 5.82%, found: 5.70%. F—calculated: 11.84%, found: 11.84%. Cl—calculated: 7.36%, found: 7.41%. $Cl^-$—calculated: 7.36%, found: 7.26%.

EXAMPLE 16

9.00 g of 3,4,5-trimethoxybenzyl chloride and 8.20 g of N-(3,4-methylenedioxyphenyl)-piperazine and 10.00 g of $K_2CO_3$ are reacted and processed according to example 14.

13.00 g of N-(3,4,5-trimethoxy-benzyl)-N'-(3,4-methylene dioxyphenyl)-piperazine dihydrochloride is obtained. Mp.: 235° C.

Elementary analysis: C—calculated: 54.90%, found: 52.86%. H—calculated: 6.14%, found: 6.22%. N—calculated: 6.09%, found: 5.87%. Cl—calculated: 15.43%, found: 14.70%.

EXAMPLE 17

13.50 g of 3,4,5-trimethoxybenzyl chloride, 17.31 g of N-(3,4,5-trimethoxyphenyl)-piperazine and 15.00 g of $K_2CO_3$ are reacted and processed according to example 14.

10.00 g of N-(3,4,5-trimethoxy-benzyl)-N'-(3,4,5-trimethoxyphenyl)-piperazine hydrochloride is obtained. Mp.: 216° C.

Elementary analysis: C—calculated: 58.90%, found: 58.73%. H—calculated: 7.09%, found: 7.09%. N—calculated: 5.97%, found: 5.95%. Cl—calculated: 7.56%, found: 7.46%.

EXAMPLE 18

9.00 g of 3,4,5-trimethoxybenzyl chloride, 11.92 g of N-(3,4-di-trifluoromethylphenyl)-piperazine and 10.00 g of $K_2CO_3$ are reacted and processed according to example 14.

14.2 g of N-(3,4,5-trimethoxybenzyl)-N'-(3,5-di-trifluoromethylphenyl)piperazine hydrochloride is obtained. Mp.: 247° C.

Elementary analysis: C—calculated: 51.31%, found: 51.15%. H—calculated: 4.89%, found: 4.78%. N—calculated: 5.44%, found: 5.36%. F—calculated: 22.14%, found: 22.31%. $Cl^-$—calculated: 6.89%, found: 6.88%.

EXAMPLE 19

11.0 g of 3,4,5-trimethoxybenzyl chloride, 9.51 g of N-(2,6-dimethylphenyl)-piperazine and 7.00 g of $K_2CO_3$ are reacted and processed according to example 14.

8.6 g of N-(3,4,5-trimethoxy-benzyl)-N'-(2,6-dimethylphenyl)-piperazine hydrochloride is obtained. Mp.: 218° C.

Elementary analysis: C—calculated: 64.93%, found: 65.24%. H—calculated: 7.68%, found: 7.84%. N—calculated: 6.88%, found 6.77%. Cl—calculated: 8.73%, found: 8.12%.

EXAMPLE 20

Additional Variations

In the same manner as given in the preceding examples, additional compounds according to the invention, having further variations in the "A" moiety thereof, in particular with respect to the substituents and number of substituents in the phenyl radical comprising the Group "A", are produced from the appropriate starting materials as set forth under "Manufacturing Process", further variations being infinitely possible between the substituents designated R, R', and R", with respect to the exact radical signified thereby, the exact position in the ring, the relative positions of the substituents in the benzene ring, and with respect to the ultimate product, whether it be the free base or a selected acid addition salt thereof. Obviously, the substituents may be present in different and varying ring positions, both individually and with respect to each other when more than one substituent is present, and different substituents, such as propyl or butyl, propoxy or butoxy, and so on, may be present in one or more positions of the benzene ring, in accord with the definitions of the substituents R, R' and R" given previously, depending only upon the judicious selection of the ring positions and the substituents present in the starting reactant containing the variable moiety "A", as set forth previously under "Manufacturing Process" herein, as well as the selection of the final form of the product, that is, whether it will be in the form of a free base or in the form of a selected acid addition salt thereof and, if to be in the form of an acid addition salt thereof, which particular salt, and whether of an organic or of an inorganic nature, all of which will immediately be apparent and within the ability of one skilled in the art.

When isolating these and other compounds of Formula I in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, and maleates of the amines of Formula I. Other acids are likewise suitable and may be employed if desired. For example, fumaric, benzoic, ascorbic, succinic, salicylic, bismethylenesalicylic, propionic, gluconic, malic, malonic, mandelic, cinnamic, citraconic, stearic, palmitic, itaconic, glycolic, benzenesulphonic, and sulphamic acids may also be employed as acid addition salt-forming acids.

In the foregoing Formula I and elsewhere herein, the term "lower-alkyl", and the lower-alkyl radical present in the term "lower-alkoxy", refers to alkyl radicals containing up to and including eight (8) carbon atoms, and preferably no more than four (4) carbon atoms. The radicals may have either straight or branched chain structure. Typical examples are methyl, ethyl, propyl, isopropyl, butyl, isobutyl, amyl, hexyl, heptyl, octyl, or the like.

PHARMACOLOGY

The compounds of the invention possess beneficial pharmacological properties, and are effective pharmaceutical agents. The compounds exhibit a circulation-stimulating effect.

The circulation-enhancing activity of the substances according to the invention can be demonstrated by known methods. One of these methods is the measurement of cerebrovascular resistance on the rabbit according to H. Hutten and P. Vaupel (cf. die Medizinische Welt 28, 1567, 1977). The therapeutic effect is expressed in terms of decrease in vascular resistance.

For this purpose 0.1 ml of a 1% solution of the test substance, i.e., according to the invention, was administered to the rabbit by arterial application. The decrease in vascular resistance (R) and the relative decrease in vascular resistance (ΔR%) were recorded and expressed in mm Hg min/l or in the valid S.I. unit k Pa min/ml, i.e., absolute decrease of resistance x time.

From Arch. Int. Pharmacodyn. Ther. 204, 37 (1973), the use of Cinnarizine as a circulation-stimulating agent is already known. The activity of this compound was tested by means of the aforementioned method. Comparative tests have however demonstrated that the N-(trimethoxybenzyl)-piperazines according to the invention show an incomparably higher decrease in vascular resistance (ΔR%), as can be observed from the following Tables, wherein the test results in comparison with Cinnarizine are given.

TABLE 1

(Examples 1-13)

| Compound according to the invention R (R' and R'' = H) | Absolute decrease of vascular resistance R (mm Hg min/l) | ΔR % |
|---|---|---|
| Compound of comparison (Cinnarizine) | 2,9 | 19,3 |
| p. Fluoro- | 4,6 | 26,4 |
| m. Methoxy- | 3,0 | 28,5 |
| o. Fluoro- | 3,0 | 23,0 |
| o. Chloro- | 3,0 | 27,9 |
| o. Methyl- | 3,3 | 24,5 |
| m. Methyl- | 3,2 | 22,0 |
| p. Methyl- | 3,3 | 23,0 |
| o. Ethyl- | 3,0 | 21,7 |
| o. Ethoxy- | 2,85 | 20,4 |
| p. Hydroxy- | 2,8 | 19,5 |
| o. Nitro- | 3,1 | 20,6 |
| o. Methoxy- | 2,94 | 22,2 |
| p. Methoxy- | 3,90 | 27,8 |

The Table shows that the N-(trimethoxybenzyl)-N'-(monosubstituted phenyl)-piperazines according to the invention effect an incomparably higher decrease of vascular resistance than the substance of comparison.

The following Table 2 shows the mean effective ED$_{50}$ and LD$_{50}$ values as well as the therapeutic indices of the piperazines according to the invention in comparison with the Cinnarizine values:

TABLE 2

(Examples 1-13)
The calculation of the therapeutic indices was based on the respective i.v. toxicities:

| Substance R (R' and R'' = H) | ED$_{50}$ mg/kg | LD$_{50}$ mg/kg | $\frac{LD_{50}}{ED_{50}}$ |
|---|---|---|---|
| Cinnarizine as comparison | 0,6 | 670 | 1110 |
| p. Fluoro- | 0,37 | 580 | 1570 |
| m. Methoxy- | 0,42 | 850 | 2010 |
| o. Fluoro- | 0,40 | 920 | 2280 |
| o. Chloro- | 0,38 | 810 | 2130 |
| o. Methyl- | 0,48 | 700 | 1450 |
| m. Methyl- | 0,46 | 700 | 1520 |
| p. Methyl- | 0,44 | 720 | 1630 |
| o. Ethyl- | 0,40 | 900 | 2240 |
| o. Ethoxy- | 0,45 | 900 | 1990 |
| p. Hydroxy- | 0,45 | 1260 | 2800 |
| o. Nitro- | 0,50 | 650 | 1300 |
| o. Methoxy- | 0,42 | 1150 | 2750 |
| p. Methoxy- | 0,30 | 910 | 3050 |

TABLE 3

(Examples 1-13)
Acute toxicities LD$_{50}$ (mouse oral) mg/kg

| Substance R | 24 h mg/kg | 14 days mg/kg |
|---|---|---|
| p. Fluoro- | 349,6 | 274,9 |
| m. Methoxy- | 410,7 | 285,2 |
| o. Chloro- | 294,8 | 255,2 |
| m. Methyl- | 452,5 | 310,3 |
| p. Methyl- | 458,6 | 312,1 |
| o. Methyl- | 456,7 | 310,8 |
| o. Ethyl- | 456,2 | 311,0 |
| o. Ethoxy- | 410,7 | 266,2 |
| p. Hydroxy- | 306,2 | 244,8 |
| o. Nitro- | 273,7 | 200,8 |

TABLE 4

(Examples 14-19)

| Compound according to the invention | Absolute decrease in vascular resistance R (mm Hg min/l) | ΔR % |
|---|---|---|
| Compound of comparison (Cinnarizine) | 2.9 | 19.3 |
| (1) N—(3,4,5-trimethoxy-benyzyl)-N'—(3,4-dimethylphenyl)-piperazine | 3.0 | 24.3 |
| (2) N—(3,4,5-trimethoxy-benzyl)-N'—(3-trifluoromethyl-4-chlorophenyl)-piperazine | 3.5 | 26.3 |
| (3) N—(3,4,5-trimethoxy-benzyl)-N'—(3,4-methylenedioxy-phenyl)-piperazine | 3.1 | 22.0 |
| (4) N—(3,4,5-trimethoxy-benzyl)-N'—(3,4,5-trimethoxy-phenyl)-piperazine | 3.0 | 21.5 |
| (5) N—(3,4,5-trimethoxy-benzyl)-N'—(3,5-di-trifluoromethyl-phenyl)-piperazine | 3.3 | 20.6 |
| (6) N—(3,4,5-trimethoxy-benzyl)-N'—(2,6-dimethyl-phenyl)-piperazine | 3.2 | 23.0 |

The therapeutic range of the substances according to the invention can again be described as excellent, since the LD$_{50}$ values lie in a favorable range, as is shown by the results of acute toxicity tests on the mouse after oral application.

TABLE 5

(Examples 14-19)
Acute toxicity oral (mouse) LD$_{50}$

| No. of substance | 24 h mg/kg | 14 days mg/kg |
|---|---|---|
| 1 | 347.9 | 263.3 |
| 2 | 328.3 | 283.2 |
| 3 | 312.1 | 296.0 |

TABLE 5-continued (Examples 14–19)
Acute toxicity oral (mouse) $LD_{50}$

| No. of substance | 24 h mg/kg | 14 days mg/kg |
|---|---|---|
| 4 | 347.7 | 347.7 |
| 5 | 300.1 | 280.2 |
| 6 | 347.7 | 264.7 |

TABLE 6

(Examples 14–19)

| No. of substance | $ED_{50}$ mg/kg | $LD_{50}$ mg/kg | Ther. Index |
|---|---|---|---|
| Cinnarizine as comparison | 0.6 | 670 | 1110 |
| 1 | 0.02 | 260 | 13000 |
| 2 | 0.09 | 283 | 3150 |
| 3 | 0.11 | 297 | 2700 |
| 4 | 0.05 | 350 | 7000 |
| 5 | 0.05 | 280 | 5600 |
| 6 | 0.07 | 265 | 3800 |

COMPOSITIONS AND METHOD OF TREATING

The novel compounds of the present invention are usually preferably employed in the form of their pharmaceutically-acceptable acid addition salts, e.g., their hydrochlorides, hydrobromides, or the like. The salt form is generally the best form for pharmaceutical formulations. Innumerable other pharmaceutically-acceptable acid addition salts can be prepared from the free base or from another acid addition salt, e.g., the hydrochloride, in a conventional manner. One acid addition salt, even if not pharmaceutically-acceptable, can readily be converted to another salt which is pharmaceutically-acceptable in known manner, if desired. The solution of any salt, after alkalization, can be extracted with a suitable solvent, e.g., ether, and dried, as with sodium sulphate, to give a solution of the selected free base, whereafter the novel piperazine compound according to the present invention can be precipitated as a salt, preferably with a pharmaceutically-acceptable acid, for example, hydrochloric or hydrobromic acid, oxalic acid, maleic acid, citric acid, tartaric acid, sulphuric acid, methanesulphonic acid, or the like. Some forms of compositions according to the present invention, comprising a compound of the present invention together with a non-toxic pharmaceutically-acceptable carrier, in addition to the active ingredient, follow. A wide variety of pharmaceutical forms suitable for many modes of administration and dosages may be employed according to the skill of the art.

The method of the present invention comprises the administration, preferably by the oral or parenteral route, of an active circulation-enhancing compound according to the present invention, preferably in the form of a composition and including a pharmaceutically-acceptable carrier, but possibly alone, as in the case of administering the active ingredient in capsulated form, in a circulation-enhancing amount, to a mammalian subject, including a human being, in need of such circulation enhancement or stimulation. In the case of compositions, the active agents of the invention are most conveniently administered in the form of such compositions containing about 0.01 to 67%, preferably 0.04 to 12.15%, by weight of active ingredient. Numerous such formulations are representatively illustrated in U.S. Pat. No. 3,402,244. The compounds and their non-toxic salts, especially the hydrochlorides, may be advantageously employed for circulation stimulation in amounts approximating those employed for the known product Cinnarizine, a clinically-useful compound used for comparative testing as reported herein, but dosages will generally be somewhat reduced in view of the superiority of the compounds of the invention with respect to Cinnarizine. Parenteral dosages are usually less than oral dosages, but the compounds and their administration are subject to wide variations in optimum daily and unit dosages, due to variations in patient body weight, condition, and ancillary factors, so that the exact dosage, both unit and daily, will of course have to be determined according to established medical principles by the physician or veterinarian in charge. In addition, the active ingredients of the present invention or compositions containing the same may either be administered together with or include other physiologically active materials and/or medicaments, such as buffering agents, antacids, sedatives, stimulants, anticholinergics, analgesics, or the like.

The following formulations are representative for all of the pharmacologically-active compounds of the invention, and are not to be construed as limiting:

FORMULATION AND ADMINISTRATION

The present invention also relates to new preparations containing the compounds according to the invention as active components. When manufacturing the preparations according to the invention the active ingredient is incorporated in a suitable carrier, e.g., a pharmaceutical carrier. Examples for suitable pharmaceutical carriers which may be used in the formulation of the preparations according to the invention are starch, gelatin, magnesium carbonate, lactose, and malt.

The present invention also relates to liquid preparations, and examples of suitable liquid carriers are ethyl alcohol, propylene glycol, glycerin, and glucose sirup.

The preparations according to the invention will be further illustrated by the following examples:

1. Drug capsules:

Capsules containing 25 mg, 50 mg and 100 mg of the active ingredient were produced.

Typical mixtures for encapsulation:

|  | 25 mg per capsule |
|---|---|
| Active ingredient (from Examples) | 25.0 |
| Lactose | 251.7 |
| Starch | 129.0 |
| Magnesium stearate | 4.3 |
| total | 410.0 mg |

Additional capsule formulations have preferably a higher active content and are given in the following:

|  | 100 mg per capsule |
|---|---|
| Active ingredient (from Examples) | 100.0 |
| Lactose | 306.5 |
| Starch | 99.2 |
| Magnesium stearate | 4.3 |
| total | 510.0 mg |

The active ingredient chosen is preferably mixed with lactose, starch and magnesium stearate, the mixture being encapsulated.

2. Tablets:

A typical formulation for a tablet containing 50 mg of the active ingredient per tablet is the following.

This formulation may also be used for other active contents by adjusting the weight of dicalcium phosphate:

|  | 50 mg per tablet |
| --- | --- |
| Active ingredient (from Examples) | 50.0 |
| Cornstarch | 13.6 |
| Cornstarch (Paste) | 3.4 |
| Lactose | 79.2 |
| Dicalcium phosphate | 68.0 |
| Calcium stearate | 0.8 |
| total | 215.0 mg |

The adjuvants are intimately mixed with the active ingredient, the resulting mixture being subsequently granulated by using water as granulating agent. The still moist granules are passed through a sieve (inside width of mesh 2.36 cm) and dried. The dried granules are mixed with calcium stearate and pressed.

3. Injectable 2% sterile solutions:

|  | per cm³ |
| --- | --- |
| Active ingredient (from Examples) | 20 mg |
| Preservative, e.g., chlorobutanol | 0.5% weight/vol. |
| Water | if necessary |

The solution is prepared, cleared by filtration, filled into tubes or ampoules, closed and heated in an autoclave.

EXAMPLE 21

4.32 g of 3,4,5-trimethoxybenzyl chloride and 3.24 g of N-phenyl piperazine is dissolved in 50 ml of dimethyl formamide in the presence of 3.0 g of water-free soda and is boiled for 8 hours under reflux. After sucking off insoluble matter the filtrate is evaporated to dryness, the residue is dissolved in methanol. Subsequently hydrochloric acid gas is introduced in the solution and the precipitate sucked off. After drying 3.4 g of N-(3,4,5-trimethoxy-benzyl)-N'-phenyl-piperazine hydrochloride is obtained.

Anal. Calcd. %: C,69.39; H,7.18; N,7.39; Cl,9.36. Found %: C,63.44; H,7.18; N,7.35; Cl,9.27. Mp.: 260° C.

This compound is a circulation stimulant according to the Hutten and Vaupel rabbit test procedure previously discussed herein. The absolute decrease of vascular resistance R in mm. Hg. min/l which it effected was 3.0 with a decrease of vascular resistance ($\Delta$R %) of 23.2. Its oral acute toxicity in the mouse (LD$_{50}$) after 24 hours is 319.7 mg/kg and after fourteen days is 265.2 mg/kg. This compound is accordingly useful as the active ingredient in pharmaceutical compositions together with a carrier or diluent, and in the method of effecting enhancement or stimulation of circulation, both in accord with the foregoing disclosure.

It is to be understood that the invention is not to be limited to the exact details of operation or exact compounds, compositions, methods, or procedures shown and described, as obvious modifications and equivalents will be apparent to one skilled in the art.

We claim:

1. Method for the treatment of a subject in need of enhancement or stimulation of circulation, comprising the step of administering to the subject a circulation-enhancing amount of a compound selected from the group consisting of
   (a) N-(trimethoxybenzyl)-N'-phenylpiperazines having the formula:

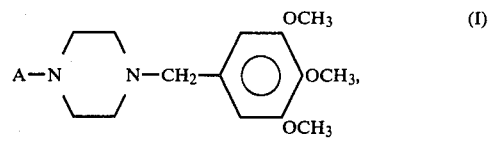

wherein A=

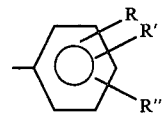

wherein
R is trifluoromethyl, hydroxy, nitro, halogen, lower-alkyl, lower-alkoxy, or hydrogen;
R' is hydrogen, trifluoromethyl, halogen, lower-alkyl, or lower-alkoxy;
R" is hydrogen or lower-alkoxy,
or wherein R and either R' or R" together stand for lower-alkylene dioxy, and
(b) pharmaceutically-acceptable acid addition salts thereof.

2. The method of claim 1, wherein the compound is N-(3,4,5-trimethoxy-benzyl)-N'-phenylpiperazine or an acid addition salt thereof.

3. Method for the treatment of a subject in need of enhancement or stimulation of circulation, comprising the step of administering to the subject a circulation-enhancing amount of a compound selected from the group consisting of
   (a) N-(trimethoxybenzyl)-N'-phenylpiperazines having the formula:

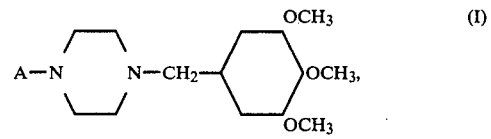

wherein A=

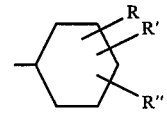

wherein
R is trifluoromethyl, hydroxy, nitro, halogen, lower-alkyl, or lower-alkoxy;
R' is hydrogen, trifluoromethyl, halogen, lower-alkyl, or lower-alkoxy;
R" is hydrogen or lower-alkoxy,
or wherein R and either R' or R" together stand for lower-alkylene dioxy, and
(b) pharmaceutically-acceptable acid addition salts thereof.

4. Method of claim 3, wherein a pharmaceutically-acceptable acid addition salt of a piperazine compound is employed.

5. The method of claim 3, wherein at least one of R' and R" is other than hydrogen.

6. The method of claim 3, wherein R is selected from the group consisting of trifluoromethyl, lower-alkoxy, halogen, hydroxy, and nitro.

7. The method of claim 3, wherein R is fluoro or chloro.

8. The method of claim 3, wherein R is lower-alkoxy.

9. The method of claim 3, wherein R is trifluoromethyl.

10. A method of claim 3, wherein lower-alkyl and lower-alkoxy contain up to and including four (4) carbon atoms.

11. A method of claim 4, wherein lower-alkyl and lower-alkoxy contain up to and including four (4) carbon atoms.

12. A method of claim 5, wherein lower-alkyl and lower-alkoxy contain up to and including four (4) carbon atoms.

13. A method of claim 6, wherein lower-alkyl and lower-alkoxy contain up to and including four (4) carbon atoms.

14. A method of claim 7, wherein lower-alkyl and lower-alkoxy contain up to and including four (4) carbon atoms.

15. A method of claim 8, wherein lower-alkyl and lower-alkoxy contain up to and including four (4) carbon atoms.

16. A method of claim 9, wherein lower-alkyl and lower-alkoxy contain up to and including four (4) carbon atoms.

17. The method of claim 3 wherein the compound is N-(3,4,5-trimethoxybenzyl)-N'-(4-fluorophenyl)-piperazine or an acid addition salt thereof.

18. The method of claim 3 wherein the compound is N-(3,4,5-trimethoxybenzyl)-N'-(2-methylphenyl)-piperazine or an acid addition salt thereof.

19. The method of claim 3 wherein the compound is N-(3,4,5-trimethoxybenzyl)-N'-(3-methoxyphenyl)-piperazine or an acid solution salt thereof.

20. The method of claim 3 wherein the compound is N-(3,4,5-trimethoxybenzyl)-N'-(2-ethylphenyl)-piperazine or an acid addition salt thereof.

21. The method of claim 3 wherein the compound is N-(3,4,5-trimethoxybenzyl)-N'-(2-ethoxyphenyl)-piperazine or an acid addition salt thereof.

22. The method of claim 3 wherein the compound is N-(3,4,5-trimethoxybenzyl)-N'-(2-nitrophenyl)-piperazine or an acid addition salt thereof.

23. The method of claim 3 wherein the compound is N-(3,4,5-trimethoxybenzyl)-N'-(4-hydroxyphenyl)-piperazine or an acid addition salt thereof.

24. The method of claim 3 wherein the compound is N-(3,4,5-trimethoxybenzyl)-N'-(2-chlorophenyl)-piperazine or an acid addition salt thereof.

25. The method of claim 3 wherein the compound is N-(3,4,5-trimethoxybenzyl)-N'-(2-methoxyphenyl)piperazine or an acid addition salt thereof.

26. The method of claim 3 wherein the compound is N-(3,4,5-trimethoxybenzyl)-N'-(4-methoxyphenyl)-piperazine or an acid addition salt thereof.

27. The method of claim 3 wherein the compound is N-(3,4,5-trimethoxybenzyl)-N'-(2-fluorophenyl)-piperazine or an acid addition salt thereof.

28. The method of claim 3 wherein the compound is N-(3,4,5-trimethoxybenzyl)-N'-(3-methylphenyl)-piperazine or an acid addition salt thereof.

29. The method of claim 3 wherein the compound is N-(3,4,5-trimethoxybenzyl)-N'-(4-methylphenyl)-piperazine or an acid addition salt thereof.

30. The method of claim 3 wherein the compounds is N-(3,4,5-trimethoxybenzyl)-N'-(3,4-dimethylphenyl)-piperazine or an acid addition salt thereof.

31. The method of claim 3 wherein the compound is N-(3,4,5-trimethoxybenzyl)-N'-(3-trifluoromethyl-4-chlorophenyl)-piperazine or an acid addition salt thereof.

32. The method of claim 3 wherein the compound is N-(3,4,5-trimethoxybenzyl)-N'-(3,4-methylenedioxyphenyl)-piperazine or an acid addition salt thereof.

33. The method of claim 3 wherein the compound is N-(3,4,5-trimethoxybenzyl)-N'-(3,4,5-trimethoxyphenyl)-piperazine or an acid addition salt thereof.

34. The method of claim 3 wherein the compound is N-(3,4,5-trimethoxybenzyl)-N'-(3,5-di-trifluoromethylphenyl)-piperazine or an acid addition salt thereof.

35. The method of claim 3 wherein the compound is N-(3,4,5-trimethoxybenzyl)-N'-(2,6-dimethylphenyl)-piperazine or an acid addition salt thereof.

36. The method of claim 4 wherein the compound is a hydrochloride acid addition salt.

* * * * *

UNITED STATES PATENT AND TRADEMARK OFFICE
CERTIFICATE OF CORRECTION

PATENT NO. : 4,370,330

DATED : January 25, 1983

INVENTOR(S) : Arthur Scherm and Dezsoe Peteri

It is certified that error appears in the above-identified patent and that said Letters Patent is hereby corrected as shown below:

Notice of References Cited, attachment to Paper 4 - July 6, 1982
Col. 3, line 30; insert after "basic" the word -- reaction --
Col. 6, line 45; "-benzoyl)-" should read -- -benzyl)- --
Col. 7, line 50; "N-(3,4-di-" should read --N-(3,5-di- --
Col. 14, approximately lines 41 and 50 (Claim 3, the formula);

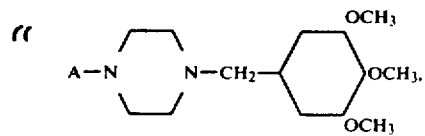

should read

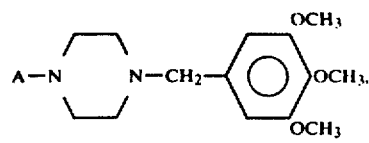

wherein A = wherein A =

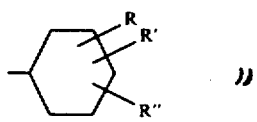

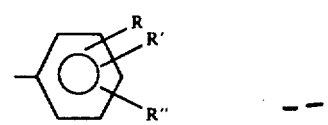

UNITED STATES PATENT AND TRADEMARK OFFICE
CERTIFICATE OF CORRECTION

PATENT NO. : 4,370,330

DATED : January 25, 1983

INVENTOR(S) : Arthur Scherm and Dezsoe Peteri

It is certified that error appears in the above-identified patent and that said Letters Patent is hereby corrected as shown below:

Col. 15, line 39; "solution" should read -- addition --
Col. 16, lines 11 & 12; "-(2-methoxyphenyl)piperazine" should read -- -(2-methoxyphenyl)-piperazine --
Col. 16, line 25; "compounds" should read -- compound -- Preliminary Signed and Sealed this Twentieth Day of September 1983

[SEAL]

Attest:

GERALD J. MOSSINGHOFF

Attesting Officer

Commissioner of Patents and Trademarks